(12) United States Patent
Bogan, Jr.

(10) Patent No.: US 9,540,300 B2
(45) Date of Patent: Jan. 10, 2017

(54) THERMAL SALT-SPLITTING OF (ALKYL)AMMONIUM 3-HYDROXYPROPIONATE

(71) Applicant: DOW GLOBAL TECHNOLOGIES LLC, Midland, MI (US)

(72) Inventor: Leonard E. Bogan, Jr., Midland, MI (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/777,027

(22) PCT Filed: Mar. 13, 2014

(86) PCT No.: PCT/US2014/025319
§ 371 (c)(1),
(2) Date: Sep. 15, 2015

(87) PCT Pub. No.: WO2014/151266
PCT Pub. Date: Sep. 25, 2014

(65) Prior Publication Data
US 2016/0031785 A1 Feb. 4, 2016

Related U.S. Application Data

(60) Provisional application No. 61/788,707, filed on Mar. 15, 2013.

(51) Int. Cl.
*C07C 59/00* (2006.01)
*C07C 51/02* (2006.01)
*C07C 51/09* (2006.01)

(52) U.S. Cl.
CPC .............. *C07C 51/02* (2013.01); *C07C 51/09* (2013.01)

(58) Field of Classification Search
None
See application file for complete search history.

(56) References Cited

U.S. PATENT DOCUMENTS

2010/0099910 A1    4/2010  Meng et al.

FOREIGN PATENT DOCUMENTS

DE    2718363    10/1978

OTHER PUBLICATIONS

International Search Report and Written Opinion for Related PCT Application PCT/US2014/025319, mailed Jul. 24, 2014 (13 pgs).

*Primary Examiner* — Patrick Lewis
(74) *Attorney, Agent, or Firm* — Brooks, Cameron & Huebsch, PLLC

(57) ABSTRACT

A salt-splitting liquid (SSL) and a process that uses the SSL to "split" (alkyl)ammonium 3-hydroxypropionate salts into ammonia (or amines) and 3-hydroxypropionic acid (3-HP) that minimizes increases in viscosity and condensation reactions of the 3-HP. Converting (alkyl)ammonium 3-hydroxypropionate in an aqueous mixture to 3-HP includes admixing a polar aprotic organic solvent and an azeotroping solvent with the aqueous mixture. The azeotroping solvent forms an azeotrope mixture with water of the aqueous mixture. The SSL is heated to convert the (alkyl)ammonium 3-hydroxypropionate to 3-HP and ammonia, where heating produces a vapor phase containing at least water, ammonia and the azeotroping solvent. At least a portion of the water and the ammonia is removed from the vapor phase during the heating, and at least a portion of the azeotroping solvent is returned from the vapor phase back to SSL to maintain the azeotrope mixture with the water.

18 Claims, No Drawings

US 9,540,300 B2

THERMAL SALT-SPLITTING OF (ALKYL)AMMONIUM 3-HYDROXYPROPIONATE

This application is a National Stage Application under 35 U.S.C. §371 of International Application Number PCT/US2014/025319, filed Mar. 13, 2014 and published as WO 2014/151266 on Sep. 25, 2014 which claims the benefit to U.S. Provisional Application 61/788,707, filed Mar. 15, 2013, the entire contents of which are incorporated herein by reference in its entirety.

TECHNICAL FIELD

The present disclosure relates to a process for converting an (alkyl)ammonium 3-hydroxypropionate to 3-hydroxypropionic acid.

BACKGROUND

The process of producing 3-hydroxypropionic acid (3-HP) involves fermenting sugar(s) at or near neutral pH. Keeping the fermentation at or near neutral pH, however, leads to formation of a salt of 3-HP, most commonly an (alkyl)ammonium 3-hydroxypropionate. Examples of such salts of 3-HP include ammonium 3-hydroxypropionate (A3HP), along with those having a mono-, di-, or tri-alkyl ammonium cation, for example a methyl-, a dimethyl-, or a trimethyl ammonium cation. In order to arrive at the 3-HP, the A3HP salt from the fermentation process needs to be "split" into ammonia and 3-HP. Once split, the ammonia is recycled and the 3-HP is converted to a more useful product, e.g. acrylic acid.

There are, however, problems in "splitting" the A3HP salt into ammonia and 3-HP. For example, in one approach to "splitting" the A3HP salt an aqueous solution of A3HP is heated at either atmospheric or reduced pressure in a process called "thermal salt-splitting" (TSS). TSS removes water from the aqueous solution, which is undesirable for two reasons: 1) the viscosity of the resulting solution increases to the point where it is very difficult to handle, and 2) the resulting 3-HP product can undergo condensation reactions both with itself (to form, e.g., oligomeric esters) and with other acids and amines present in the mixture, such as acetic and glutamic acids. These condensation reactions complicate both the subsequent dehydration reaction and the separation processes. Reactions with amines to form amides are especially undesirable as it is difficult to convert these products to acrylic acid.

There is a need, therefor, in the art for a salt-splitting liquid and a process that uses the salt-splitting liquid to "split" the A3HP salt into ammonia and 3-HP that minimizes any increase in the viscosity and the condensation reactions of the 3-HP. There is a need, therefor, in the art for a process that minimizes any increase in the viscosity and the condensation reactions of the 3-HP.

SUMMARY

The present disclosure provides for a salt-splitting liquid and a process that uses the salt-splitting liquid to "split" the (alkyl)ammonium 3-hydroxypropionate salt into ammonia and 3-hydroxypropionic acid (3-HP) and that minimizes both increases in the viscosity and the condensation reactions of the 3-HP. Specifically, the present disclosure provides, among other things, a process of converting (alkyl)ammonium 3-hydroxypropionate in an aqueous mixture to 3-HP. The process includes admixing a polar aprotic organic solvent with the aqueous mixture, where the (alkyl)ammonium 3-hydroxypropionate and the 3-HP are soluble in the polar aprotic organic solvent. An azeotroping solvent is admixed with the aqueous mixture and the polar aprotic organic solvent, where the azeotroping solvent forms an azeotrope mixture with the water of at least the aqueous mixture. The aqueous mixture, polar aprotic solvent, and azeotroping solvent together form the salt-splitting liquid. The salt-splitting liquid is heated to convert the (alkyl)ammonium 3-hydroxypropionate to 3-HP and ammonia, where heating the salt-splitting liquid also produces a vapor phase containing at least water, ammonia and the azeotroping solvent. At least a portion of the water and the ammonia is removed from the vapor phase during the heating. At least a portion of the azeotroping solvent from the vapor phase is returned back to the salt-splitting liquid to maintain the azeotrope mixture with the water of at least the aqueous mixture. Returning at least a portion of the azeotroping solvent from the vapor phase back to the salt-splitting liquid includes maintaining a 0.1 weight percent (wt. %) to 1 wt. % of the azeotroping solvent in the salt-splitting liquid based on the total weight of the salt-splitting liquid. The (alkyl)ammonium 3-hydroxypropionate can be ammonium 3-hydroxypropionate (A3HP).

Heating the salt-splitting liquid can be to a temperature of 100° C. to 200° C. The azeotroping solvent is selected from the group consisting of toluene, m-xylene, anisole, methyl isobutyl ketone, benzene, cyclohexane, diethyl ether, methyl ethyl ketone or a combination thereof. The polar aprotic organic solvent is selected from the group consisting of dimethylformamide (DMF), dimethylacetamide (DMA), N-methyl-2-pyrrolidone (NMP), dimethyl sulfoxide (DMSO), dimethylsulfone, dioxane, diglyme, or a combination thereof. The polar aprotic organic solvent is admixed with the aqueous mixture so that a weight ratio of 3-HP to polar aprotic organic solvent (3-HP:polar aprotic organic solvent) in the aqueous mixture is 0.6:1 or lower, preferably 0.18:1 to 0.58:1, more preferably 0.24:1 to 0.42:1.

DETAILED DESCRIPTION

Fermentation broths used in the production of 3-hydroxypropionic acid (3-HP) operate at or near neutral pH. In maintaining this neutral pH salts of the 3-HP are produced (e.g., (alkyl)ammonium 3-hydroxypropionate), most commonly ammonium 3-hydroxypropionate (A3HP). So to arrive at the 3-HP, ammonia is "split" from the (alkyl)ammonium 3-hydroxypropionate.

A direct method of "splitting" the (alkyl)ammonium 3-hydroxypropionate, such as A3HP, into ammonia and 3-HP is to heat the aqueous mixture in a "thermal salt-splitting" or "TSS" process. During the heating, the (alkyl)ammonium 3-hydroxypropionate converts to 3-HP as ammonia and water are removed. The heating process also causes an increase in both the acidity of the aqueous mixture (e.g., the aqueous mixture becoming more acidic) and the concentration of 3-HP in the aqueous mixture as ammonia and water are removed. This condition can cause the 3-HP to undergo further reactions to give not only 3-HP ester oligomers, but also other reaction products.

In DE 2718363 it was suggested that the heating process can be used with ammonium salts of carboxylic acids (e.g., isobutyrate, acetate, adipate, (meth)acrylate, benzoate, and terephthalate) in water-soluble organic solvents (e.g., dimethylformamide (DMF), dimethylacetamide (DMA), N-methylpyrrolidone (NMP), dimethylsulfoxide (DMSO), dimethylsulfone, dioxane, and diglyme). U.S. Pat. Pub. No. 2010/0099910 suggests that the heating of a β-hydroxycarboxylic acid can be accomplished in a single phase in a non-aqueous solvent. Examples from this publication describe heating A3HP in NMP to give 91% and 94% conversion of A3HP to 3-HP.

There are several problems, however, with the approaches of DE 2718363 and U.S. Pat. Pub. No. 2010/0099910. For example, the solvents in DE 2718363 work well at low concentrations of salt in solvent (e.g., low concentrations being 0.2 mole of salt in 100 grams of solvent, or a 3-HP/solvent ratio of 0.18). It is, however, desirable to work at higher 3-HP concentrations for an industrial process (e.g., 3-HP concentrations from 18 weight percent (wt. %) to as high as 60 wt. % based on the total weight of the entire solution (e.g., the salt-splitting solution)). The solvent NMP used in U.S. Pat. Pub. No. 2010/0099910 works well at higher concentrations of salt, but subsequent separation of 3-HP from the solvent is difficult because the solvent has a boiling point that is high at standard temperature and pressure (e.g., 202° C.), and the basic nature of the NMP solvent will militate against separation from the acidic 3-HP. Furthermore, use of the lower boiling solvents listed in DE 2718363 (e.g., DMF, DMA and DMSO) leads to severe foaming problems that render them unfit for use in a commercial process.

The present disclosure provides a solution to these issues. Surprisingly it has been discovered that the addition of an azeotroping solvent and a polar aprotic organic solvent to an aqueous mixture containing an (alkyl)ammonium 3-hydroxypropionate, such as A3HP, forms an azeotrope mixture with the water that not only enables removal of water from the aqueous mixture at a reduced temperature, but also promotes removal of ammonia to a higher degree (higher conversion of salt to ammonia and acid). It has also been surprisingly discovered that the use of the azeotroping solvent in the aqueous mixture also mitigates the foaming problems encountered during the heating process (e.g., thermal salt-splitting) with many polar aprotic organic solvents.

As used herein, an "aqueous mixture" can be derived from a fermentation broth or can be the product medium resulting from subjection of microorganisms to one or more fermentation stages in a fermentation medium to produce, among other things, 3-hydroxypropionic acid (3-HP) and a salt of 3-HP, e.g., (alkyl)ammonium 3-hydroxypropionate, most commonly ammonium 3-hydroxypropionate (A3HP) aqueous mixture. The fermentation medium, as used herein, means a mixture of water, sugars and dissolved solids that is used in one or more fermentation stages allow microorganisms to produce 3-HP and A3HP, along with other compounds. The aqueous mixture may be subjected to pasteurization, sterilization, purification, filtration, concentration, or a combination thereof. Suitable examples of an aqueous mixture, as used herein, include, but are not limited to, those described in International Publication Number WO 2011/094457, incorporated herein by reference in its entirety.

As used herein, the term "ammonium" (e.g., as in ammonium 3-hydroxypropionate) refers to a cation having the formula $NHR_3^+$ where each R group, independently, is hydrogen or a substituted or unsubstituted alkyl, aryl, aralkyl, or alkoxy group. Preferably, each of the R groups is hydrogen.

As used herein, a "salt-splitting liquid" can have the physical characteristic of being either a mixture or a solution, as are known in the art. The aqueous mixture, polar aprotic solvent, and azeotroping solvent together form the salt-splitting liquid.

As used herein, "thermal salt-splitting" is a process used to "split" or "convert" (alkyl)ammonium 3-hydroxypropionate, such as A3HP, to 3-HP and ammonia. The thermal salt-splitting process includes heating the salt-splitting liquid that includes the aqueous mixture to convert (alkyl) ammonium 3-hydroxypropionate, such as A3HP, to 3-HP and ammonia. As such, heating the salt-splitting liquid to convert (alkyl)ammonium 3-hydroxypropionate, such as A3HP, to 3-HP and ammonia is a thermal salt-splitting process.

The process of the present disclosure converts (alkyl) ammonium 3-hydroxypropionate, e.g., A3HP, in the aqueous mixture to 3-HP. The process includes admixing a polar aprotic organic solvent with the aqueous mixture, where the (alkyl)ammonium 3-hydroxypropionate and the 3-HP are soluble in the polar aprotic organic solvent. An azeotroping solvent is admixed with the aqueous mixture and the polar aprotic organic solvent. The azeotroping solvent forms an azeotrope mixture with the water of at least the aqueous mixture. As used herein, an azeotroping solvent is a liquid that forms an azeotrope with the water. The (alkyl)ammonium 3-hydroxypropionate can be A3HP.

The salt-splitting liquid is heated to convert the (alkyl) ammonium 3-hydroxypropionate, e.g., A3HP, into 3-HP and ammonia (e.g., TSS). Heating the salt-splitting liquid also produces a vapor phase containing at least water, ammonia and the azeotroping solvent. At least a portion of the water and the ammonia are removed from the vapor phase during the heating and at least a portion of the azeotroping solvent is returned from the vapor phase back to salt-splitting liquid to maintain the azeotrope mixture with the water of the aqueous mixture.

As used herein, soluble means the ability of (alkyl) ammonium 3-hydroxypropionate ammonium, e.g. A3HP, and the 3-HP, at the concentrations provided herein, to mix with the polar aprotic organic solvent and the aqueous mixture to form a homogeneous solution (e.g., the aqueous solution of the aqueous mixture). This allows for the solubility of the (alkyl)ammonium 3-hydroxypropionate, e.g., A3HP, the 3-HP and the polar aprotic organic solvent in the aqueous mixture (e.g., water, among other compounds). From this homogeneous solution the water and the ammonia can be separated (via the vapor phase), leaving the polar aprotic organic solvent in the salt-splitting liquid. Maintaining the polar aprotic organic solvent in the salt-splitting liquid helps to keep the viscosity of the aqueous mixture low enough (e.g., less than 5000 centiPoise (cP), preferably less than 2000 cP, measured at 25° C.) to allow the salt-splitting liquid to be handled more easily. Maintaining the solvent in the salt-splitting liquid also helps to keep the 3-HP dilute (e.g., a concentration of about 6.3 mole of 3-HP per liter of salt-splitting liquid or less) so as to minimize side and polymerization reactions. As such, the present disclosure provides for, among other things, a polar aprotic organic solvent and an azeotroping solvent that, when used with an aqueous mixture during heating (e.g., thermal salt-splitting), allow for the solubility of water, 3-HP and the (alkyl) ammonium 3-hydroxypropionate, e.g., A3HP, in the salt-splitting liquid, the separation of the water and ammonia in the vapor phase, and the polar aprotic organic solvent to remain in the salt-splitting liquid of the aqueous mixture to keep the system viscosity low enough to handle the material and keep the 3-HP dilute enough to minimize side and polymerization reactions.

Preferably, the polar aprotic organic solvent has a boiling point that is higher than, but close to, that of water (at comparable pressure and temperature). This allows the water to be preferentially removed during the heating process and also facilitates its removal later in the process. As discussed, the water, 3-HP and the (alkyl)ammonium 3-hydroxypropionate, e.g., A3HP, are all soluble in the polar aprotic solvent (e.g., the polar aprotic solvent is a good solvent for the aqueous mixture). As discussed, the aqueous mixture can be "concentrated" (e.g., where water has been removed from the aqueous mixture prior to the addition of the polar aprotic solvent, such as by rotary evaporation) so as to provide a concentrated aqueous mixture to be used with the present disclosure.

The polar aprotic organic solvent can be one that dissolves both 3-HP and the (alkyl)ammonium 3-hydroxypropionate, such as A3HP, in the required proportions. Examples of the polar aprotic organic solvent include, but are not limited to, those selected from the group consisting of dimethylformamide (DMF), dimethylacetamide (DMA), N-methylpyrrolidone (NMP), dimethylsulfoxide (DMSO), dimethylsulfone, dioxane, diglyme, or a combination thereof.

Determining the amount of polar aprotic organic solvent to admix with the aqueous mixture is based on an assumption that water will be completely removed from the salt-splitting liquid by the end of the process of the present disclosure. The amount of polar aprotic organic solvent to use is, therefore, a function of the desired concentration (e.g., wt. %) of the 3-HP in the polar aprotic organic solvent and the azeotroping solvent, as provided herein, at the end of the process. This can also be function of the weight ratio of the 3-HP to the polar aprotic organic solvent.

For the various embodiments, polar aprotic organic solvent is admixed with the aqueous mixture so that a weight ratio of 3-HP to polar aprotic organic solvent (3-HP:polar aprotic organic solvent) in the aqueous mixture is 0.6:1 or lower, preferably 0.18:1 to 0.58:1, more preferably 0.24:1 to 0.42:1. Another approach to how much of the polar aprotic organic solvent is admixed with the aqueous mixture is to have a concentration of up to 60 weight percent (wt. %) of the 3-HP in the salt-splitting liquid, preferably 10 to 40 wt. % of the 3-HP in the salt-splitting liquid, more preferably 11 to 26 wt. % of the 3-HP in the salt-splitting liquid. It is also possible that the 3-HP in the salt-splitting liquid can have a concentration of 15 to 25 wt. % based on the total weight of the salt-splitting liquid.

An azeotroping solvent is admixed with the aqueous mixture and the polar aprotic organic solvent. As used herein, an azeotroping solvent is a liquid that forms an azeotrope with the water (an azeotrope mixture) in the aqueous mixture. This helps to lower the amount of heat needed during the conversion of the (alkyl)ammonium 3-hydroxypropionate, e.g., the A3HP, to 3-HP by lowering the temperature at which water is removed from the salt-splitting liquid. A result of admixing the azeotroping solvent is, therefore, to make the water and ammonia removal from the salt-splitting liquid more efficient. In other words, the use of the azeotroping solvent helps to achieve better removal of both the water and the ammonia from the salt-splitting liquid as compared to not using the azeotroping solvent.

The azeotroping solvent is selected from the group consisting of aromatic hydrocarbons (for example benzene, toluene, m-xylene, anisole), ketones (for example methyl isobutyl ketone, methyl ethyl ketone), alkanes (for example cyclohexane), ethers (for example diethyl ether) or a combination thereof. For example, the azeotroping solvent includes, but is not limited to, those selected from the group consisting of toluene, m-xylene, anisole, methyl isobutyl ketone, benzene, cyclohexane, diethyl ether, methyl ethyl ketone or a combination thereof.

An example of a preferred combination of the polar aprotic organic solvent and the azeotroping solvent is DMSO and toluene.

The reaction apparatus used in the process of the present disclosure can include those styled after a Dean-Stark apparatus. Generally, the reaction apparatus includes a heated reactor vessel (e.g., used to heat the salt-splitting liquid and generate the vapor phase discussed herein) having an outlet into a fractionating column structure. The heated reactor can be used to heat the salt-splitting liquid to a temperature of 100° C. to 200° C. The fractionating column structure includes a condenser and a decanter. The vapor phase produced in the heated reactor enters the condenser where it condenses and enters the decanter. In the decanter the condensed salt-splitting liquid is allowed to separate into an aqueous layer and an azeotroping solvent layer. A portion of the aqueous layer (e.g., water and ammonia) is removed while a controlled portion of the azeotroping solvent layer is returned to the salt-splitting liquid in the heated reactor so as to at least maintain the base level of azeotroping solvent in the salt-splitting liquid. The reaction apparatus can be operated at atmospheric pressure. Alternatively, the reaction apparatus can be operated at a reduced pressure (a pressure lower than atmospheric pressure, e.g., under vacuum).

As discussed, at least a portion of the water and the ammonia is removed from the vapor phase during the heating. At least a portion of the azeotroping solvent from the vapor phase is also returned back to salt-splitting liquid to maintain the azeotrope mixture with the water of the aqueous mixture. This process ensures that the azeotroping solvent is always present in the salt-splitting liquid during the heating process that converts the (alkyl)ammonium hydroxypropionate, e.g., A3HP, to 3-HP and ammonia. Preferably, the salt-splitting liquid has a base level of at least 0.1 wt. % of the azeotroping solvent based on the total weight of the salt-splitting liquid. More preferably, the salt-splitting liquid has a base level of at least 1 wt. % of the azeotroping solvent based on the total weight of the salt-splitting liquid. The base level can also be maintained at 0.1 wt. % to 1 wt. % of the azeotroping solvent in the salt-splitting liquid based on the total weight of the salt-splitting liquid.

The use of the azeotroping solvent in the aqueous mixture has also been surprisingly found to control foaming during the heating process (e.g., thermal salt-splitting) that is encountered without the use of the azeotroping solvent. It has been found that when an azeotroping solvent is not used, but the process of converting the (alkyl)ammonium 3-hydroxypropionate, such as A3HP, e.g., A3HP, to 3-HP and ammonia remains otherwise the same, foaming inside the heated reactor can create a foam that rises and fills the headspace above the salt-splitting liquid to the point that the process must be stopped prior to achieving satisfactory conversion of the (alkyl)ammonium 3-hydroxypropionate, e.g., A3HP, to 3-HP and ammonia.

The following examples are provided to illustrate the disclosure, but are not intended to limit the scope thereof.

EXAMPLES

Materials

Prepare the aqueous mixture according to Example 11A (the second fermentation) as provided in International Publication Number WO 2011/094457, incorporated herein by reference in its entirety. Concentrate the aqueous mixture to about 32 wt. % to about 53 wt. % 3-HP by evaporating water at 50° C. and 30 mm Hg on a rotary evaporator.

All other compounds were purchased from either Sigma/Aldrich or Fisher Scientific and used as supplied.

Measurement Techniques and Devices

Measure the weight percent (wt. %) of 3-HP using HPLC.

Apparatus and Procedure

Prepare the System Reactor as follows. To a 250 ml three-neck round bottom flask fit both a feed inlet (above the salt-splitting liquid surface) and a Dean-Stark trap. Equip the flask with a magnetic stir bar and a heating mantle. With the feed inlet use a peristaltic pump (Masterflex L/S) to add the aqueous mixture to the flask of the Reactor System.

For the Examples using toluene, charge the flask of the Reactor System with the polar aprotic solvent, as discussed below, and charge the Dean-Stark trap with 14 to 16 grams (g) of toluene. Add the remainder of the toluene to the flask, and heat the contents to reaction temperature as provided in the Example listed below.

For the Examples and Comparative Examples listed below the content of the flask are held at reflux temperature, where the temperature varies with the water content in the reaction mixture in the flask. The feed rate of the aqueous mixture was controlled, when needed, to prevent foam from traveling out of the flask and into the Dean-Stark trap.

Express the concentrations of ammonium 3-hydroxypropionate (A3HP) as weight percent of 3-hydroxypropionic acid (3-HP) equivalents (measure by HPLC). Determine total base by titration with 0.1 N HCl and express in total meq in the sample.

Comparative Example (Comp Ex) A—DMSO w/o Toluene: Foaming Problem, Lower Yield

Add DMSO (100.0 g, solvent) to the flask and heat to a reaction temperature of 140° C. Add aqueous mixture (55.0 g, 45.4 wt. % 3-HP, 19.8 wt. % water, 288.0 meq total base, pH=5.4) to the flask with stirring over 84 minutes. Hold the reaction temperature in the salt-splitting liquid at 133 to 145° C. during the addition of the aqueous mixture. The aqueous mixture is fed to the Reactor System quickly at first, but after several minutes foaming is so severe that the feed rate has to be reduced considerably to keep the foam from going overhead. After the addition is complete, the reaction temperature is held at 135 to 140° C. for 30 min.

The reaction products are 148.3 g total in the bottoms, containing 78.6 meq total base, corresponding to a 72.7% conversion of the A3HP, and 4.3 g of water and ammonia in the overhead.

Example (Ex) 1

DMSO w/Toluene: Little Foaming, High Yield

Add DMSO (96.4 g, solvent) and toluene (22.0 g) to the flask and heat to a reaction temperature of 140° C. Add aqueous mixture (94.0 g, 32.2 wt. % 3-HP, 40.3 wt. % water, 382.9 meq total base, pH=5.5) to the flask with stirring over 9 minutes. Hold the reaction temperature in the salt-splitting liquid at 111 to 147° C. during the addition of the aqueous mixture. After the addition is complete, the reaction temperature is held at 111 to 147° C. for 139 minutes. The reaction products are 150.2 g total in the bottoms, containing 34.5 meq total base, corresponding to a 91.0% conversion of the A3HP; and 38.5 g of water and ammonia in the overhead. NMR analysis of the product shows mostly 3-HP monomer.

Com Ex B—Dioxane: Fails to Dissolve

Add dioxane (100.0 g, solvent) to the flask and heat to a reaction temperature of about 100° C. Add aqueous mixture (58.0 g, 52.6 wt. % 3-HP, 6.9 wt. % water, 327.4 meq total base, pH=5.2) to the flask with stirring over 29 min. The reaction temperature of the salt-splitting liquid is about 100° C. during the addition of the aqueous mixture. After the addition is complete, hold the reaction temperature at about 100° C. for 2 hours. A second phase forms in the salt-splitting liquid from the start.

Comp Ex C—Triglyme/Toluene: Fails to Dissolve

Add triglyme (59.9 g, solvent) and toluene (22 g) to the flask and heat to a reaction temperature of 160° C. Add aqueous mixture (55.3 g, 32.2 wt. % 3-HP, 40.3 wt. % water, 225.2 meq total base, pH=5.5) to the flask with stirring over 14 min. Maintain the reaction temperature of the salt-splitting liquid at 118-160° C. during the addition of the aqueous mixture. Essentially no foaming occurs, but a second phase forms in the salt-splitting liquid. NMR analysis of the product shows substantial oligomerization of the 3-HP.

Ex 2

Ethylene Glycol: Addition of Toluene Enables Completion of Experiment

Add ethylene glycol (80.0 g, solvent) to the flask and heat to a reaction temperature of 148° C. Add aqueous mixture (102.8 g, 32.2 wt. % 3-HP, 40.3 wt. % water, 418.7 meq total base, pH=5.5) to the flask with stirring over 71 min. Maintain the reaction temperature of the salt-splitting liquid at 107 to 154° C. during the addition of the aqueous mixture. Initially, there is little to no foaming, but after 6 min. it is necessary to briefly stop the feed of the aqueous mixture to avoid having foam from the flask enter the Dean Stark trap.

Adding toluene (21.0 g) to the flask reduced the foam and allowed the remainder of the aqueous mixture to be added to the flask. After the addition of the aqueous mixture is complete (71 min.), the temperature is held at 107 to 154° C. for 164 min.

The reaction products are 132.0 g total in the bottoms, containing 132.5 meq total base, corresponding to a 68.4% conversion of the A3HP; and 47.9 g of water and ammonia in the overhead.

Comp Ex D—NMP w/o Toluene

Add NMP (80.0 g, solvent) to the flask and heat to a reaction temperature of 149° C. Add aqueous mixture (101.1 g, 32.2 wt. % 3-HP, 40.3 wt. % water, 411.8 meq total base, pH=5.5) to the flask with stirring over 55 min. Maintain the reaction temperature of the salt-splitting liquid from 128° C. to 157° C. during the addition of the aqueous mixture. After 13 min. it is necessary to reduce the feed rate to manage foaming, and after 17 min. it is necessary to stop the addition for 3 min. Complete addition is achieved after 55 min. After the addition is complete, the temperature is held at 128° C. to 157° C. for 180 min.

The reaction products are 129.1 g total in the bottoms, containing 16.7 meq total base, corresponding to a 96% conversion of the A3HP; and 48.5 g of water and ammonia in the overhead. NMR analysis of the product shows mostly 3-HP monomer.

Ex 3

NMP/Toluene: Less Foaming, Complete Conversion

Add NMP (80.0 g, solvent) and toluene (21.0 g) to the flask and heat to a reaction temperature of 153° C. Add aqueous mixture (103.4 g, 32.2 wt. % 3-HP, 40.3 wt. % water, 421.1 meq total base, pH-5.5) to the flask with stirring over 76 min. Maintain the temperature of the salt-splitting liquid from 113° C. to 171° C. during the addition of the aqueous mixture. After 11 min. it is necessary to reduce the feed rate to manage foaming, but the feed is never stopped. Complete addition is achieved over 76 min. After the addition is complete, the temperature is held at 128° C. to 157° C. for 95 min.

The reaction products are 132.0 g total in the bottoms, containing no observable base, corresponding to a 100.0% conversion of the A3HP; and 47.5 g of water and ammonia in the overhead.

Comp Ex E DMF

Add DMF (100 g, solvent) to the flask and heat to a reaction temperature of 144° C. Add aqueous mixture (53.6 g, 32.6 wt. % 3-HP, 41.6 wt. % water, 224.8 meq total base, pH=5.5) to the flask with stirring over 14 min., at which time the feed is stopped to manage foaming. Maintain the temperature of the salt-splitting liquid at about 123° C. during the addition of the aqueous mixture. The contents are heated to 150° C. and held at that temperature until distillation stops, about 20 min.

The reaction products are 109.7 g total in the bottoms, containing 6.14 meq total base, corresponding to a 97.3% conversion of the A3HP; and 39.1 g of water and ammonia in the overhead.

Comp Ex F DMF (an Attempt to Feed a Greater Amount of Broth to the Solvent)

Add DMF (100 g, solvent) to the flask and heat to a reaction temperature of 132° C. Add aqueous mixture (120.9 g, 47.7 wt. % 3-HP, 15.6 wt. % water, 618.8 meq total base) to the flask with stirring over 78 min. Maintain the reaction temperature of the salt-splitting liquid at about 122-140° C. during the addition of the aqueous mixture. After 8 min. the feed is stopped for 11 min. to manage foaming. Complete addition is achieved over 78 min. After addition is complete, the reaction temperature is held at 135° C. for 33 min.

The reaction products are 192.5 g total in the bottoms, containing 203.2 meq total base, corresponding to a 67.2% conversion of the A3HP; and 20.6 g of water and ammonia in the overhead.

Ex 4

DMF/Toluene: Toluene Manages Foaming, but does not Improve Conversion

Add DMF (100.0 g, solvent) and toluene (7.0 g) to the flask and heat to a reaction temperature of 117° C. Add aqueous mixture (96.45 g, 32.2 wt. % 3-HP, 40.3 wt. % water, 384.8 meq total base, pH=5.5) to the flask with stirring over 41 min. Maintain the temperature of the salt-splitting liquid at about 106-115° C. during the addition of the aqueous mixture. The feed rate is slowed after 12 min. to manage foaming, but never stopped. Complete addition is achieved over 41 min. After the addition is complete, the temperature is held at 113 to 120° C. for 15 min.

The reaction products are 163.2 g total in the bottoms, containing 172.2 meq total base, corresponding to a 55.2% conversion of the A3HP; and 35.0 g of water and ammonia in the overhead.

Comp Ex G: DMF

Add DMF (100 g, solvent) to the flask and heat to a reaction temperature of 135° C. Add aqueous mixture (56.8 g, 47.7 wt. % 3-HP, 15.6 wt. % water, 238.2 meq total base, pH=5.5) to the flask with stirring over 50 min. Maintain the reaction temperature of the salt-splitting liquid at about 135° C. during the addition of the aqueous mixture. After addition is complete, the reaction temperature is held at 140° C. for 2 hours and 45 min.

The reaction products are 113.1 g total in the bottoms, containing 11.1 meq total base, corresponding to a 95.3% conversion of the A3HP; and 38.9 g of water and ammonia in the overhead.

Comp Ex H: DMF

Add DMF (50 g, solvent) and 4 g of water to the flask and heat to a reaction temperature of 130° C. Add aqueous mixture (100 g, 52.6 wt. % 3-HP, 6.93 wt. % water, 564.5 meq total base) to the flask with stirring over 91 min. (slow addition was necessary to manage foaming). Maintain the reaction temperature of the salt-splitting liquid at about 135° C. during the addition of the aqueous mixture. After addition is complete, the reaction temperature is held at 130 to 135° C. for 5 min.

The reaction products are 179.4 g total in the bottoms, containing 208.7 meq total base, corresponding to a 63.0% conversion of the A3HP; and 7.1 g of water and ammonia in the overhead.

Comp Ex 1: DMA

Add DMA (100 g, solvent) to the flask and heat to a reaction temperature of 145° C. Add aqueous mixture (53.9 g, 45.4 wt. % 3-HP, 19.79 wt. % water, 282.2 meq total base, pH=5.4) to the flask with stirring over 16 min. Maintain the reaction temperature of the salt-splitting liquid in a range 128 to 145° C. during the addition of the aqueous mixture. After addition is complete, the reaction temperature is held at 128 to 145° C. for 20 min.

The reaction products are 135.0 g total in the overhead, containing 19.0 meq total base, corresponding to a 93.3% conversion of the A3HP; and 15.4 g of water and ammonia in the overhead.

Ex 5

DMSO/Toluene: Less Foaming, Complete Conversion

Take a 120.83 g sample of the DMSO and aqueous mixture (after addition is complete) as prepared in Comparative Example A and add toluene (24.0 g) in two 12 g aliquots to the flask and heat to a reaction temperature of about 140° C. Hold the reaction temperature in the salt-splitting liquid at about 140° C. for 3 hrs.

The reaction products are 119.4 g total in the overhead, containing 1.5 meq total base, corresponding to a 99.5% conversion of the A3HP; and 8.5 g of water and ammonia in the overhead.

Comp Ex J: NMP

Add NMP (100 g, solvent) to the flask and heat to a reaction temperature of 126 to 150° C. Add aqueous mixture (52.4 g, 45.4 wt. % 3-HP, 19.79 wt. % water, 274.3 meq total base, pH=5.4) to the flask with stirring over 15 min. Maintain the reaction temperature of the salt-splitting liquid in a range 126 to 150° C. during the addition of the aqueous mixture. After addition is complete, the reaction temperature is held at 126 to 150° C. for 21 min.

The reaction products are 140.6 g total in the overhead, containing 6.9 meq total base, corresponding to a 97.5% conversion of the A3HP; and 7.1 g of water and ammonia in the overhead.

The data in Table 1 summarize the reaction conditions and the results. The feed times listed are total time from start of feed to end (including time stopped to wait for foaming to subside). The hold times are the time at temperature after completion of the feed. The temperature varied as feed rate was varied, so the temperature column lists the entire range of temperatures recorded during an experiment.

TABLE 1

| | Solvent | Conc. 3-HP in feed (%) | 3-HP/solvent (wt. ratio) | A3HP conversion (%) | final water (%) | mass balance | water balance | feed time (min) | hold time (min) | rxn temp (° C.) |
|---|---|---|---|---|---|---|---|---|---|---|
| Comp Ex G | DMF | 32.8 | 0.19 | 95.3 | 4 | 0.969 | 0.959 | 50 | 165 | 140 |
| Comp Ex E | DMF | 32.8 | 0.18 | 97.3 | 2.2 | 0.969 | 0.961 | 14 | 20 | 123-150 |
| Comp Ex H | DMF | 52.6 | 0.53 | 63.0 | 4.1 | 0.933 | 1.02 | 91 | 5 | 130-135 |
| Comp Ex F | DMF | 47.7 | 0.58 | 67.2 | 5.6 | 0.965 | 1.155 | 78 | 33 | 122-140 |
| Comp Ex I | DMA | 45.4 | 0.24 | 93.3 | 2.2 | 0.977 | 1.047 | 16 | 20 | 128-155 |
| Comp Ex B | dioxane | 52.6 | 0.31 | | | | | 29 | 120 | 100 |
| Comp Ex C | triglyme-toluene | 32.2 | 0.30 | | | | | | | |
| Comp Ex J | NMP | 45.4 | 0.24 | 97.5 | 3 | 0.969 | 0.903 | 15 | 21 | 126-150 |
| Comp Ex D | NMP | 32.2 | 0.41 | 96.0 | 4.1 | 0.981 | 1.03 | 55 | 180 | 128-157 |
| Comp Ex A | DMSO | 45.4 | 0.25 | 72.7 | 7.9 | 0.985 | 1.079 | 84 | 30 | 133-145 |
| Ex 5 | DMSO-toluene | | | 99.5 | 2.7 | 0.986 | | 0 | 180 | |
| Ex 1 | DMSO-toluene | 32.2 | 0.31 | 91.0 | 4.4 | 0.961 | 1.192 | 9 | 139 | 111-147 |
| Ex 4 | DMF-toluene | 32.2 | 0.31 | 55.2 | 11.7 | 1.009 | 0.642 | 41 | 15 | 113-120 |
| Ex 2 | EG-toluene | 32.2 | 0.41 | 68.4 | 6.5 | 0.978 | 1.065 | 71 | 184 | 107-154 |
| Ex 3 | NMP-toluene | 32.2 | 0.42 | 100.0 | 3.1 | 0.963 | 0.988 | 76 | 95 | 113-171 |

As Table 1 shows, thermal-salt-splitting (TSS) of A3HP in DMF is efficient as long as the concentration of 3-HP is low (15-17 wt. %), but it loses effectiveness at a concentration of 24 wt. %. TSS of A3HP in DMA behaved similarly. TSS in 1,4-dioxane or triglyme resulted in a two-phase mixture at the end of the process, even though 3-HP is soluble in both solvents. A3HP is poorly soluble in those solvents, and evidently the presence of other organics and salts in the aqueous 3-HP mixture is enough to stabilize a separate aqueous phase. TSS is efficient in NMP, even at a concentration of 25 wt. %. This is likely because the amine functionality in NMP can replace ammonia as a counterion, but NMP has a significant issue in that this ion-pairing and the high boiling point of NMP (203° C.) will make later separation difficult. TSS proceeds to only about 73% conversion in DMSO, but when toluene was added to remove water as an azeotrope, very efficient removal of ammonia also resulted (Ex 5). Adding toluene to DMSO from the start (Ex 1) gave similar results. Adding toluene to DMF however resulted in less conversion. Complete removal of ammonia was observed using a mixture of NMP and toluene (Ex 3).

Ex 1 and Ex 5 demonstrated the results of using an azeotroping solvent. Conversion and water removal were both high, and foaming was manageable (e.g., Ex 1 required only nine minutes feed time) when the azeotroping solvent is used. The boiling point of DMSO (189° C.) is low enough and its stability great enough that it can be removed from the dehydration reaction, yet its boiling point is high enough that it should separate readily from acrylic acid. In contrast, the basicity of NMP would likely both prevent its distillation from the dehydration reactor and consume acid equivalents there.

While the foregoing is directed to embodiments of the disclosure, other and further embodiments of the disclosure may be devised without departing from the basic scope thereof.

I claim:

1. A process of converting an (alkyl)ammonium 3-hydroxypropionate in an aqueous mixture to 3-hydroxypropionic acid (3-HP), the process comprising:
   admixing a polar aprotic organic solvent and the aqueous mixture, where the (alkyl)ammonium 3-hydroxypropionate and the 3-HP are soluble in the polar aprotic organic solvent;
   admixing an azeotroping solvent and the aqueous mixture and the polar aprotic organic solvent, where the azeotroping solvent forms an azeotropic mixture with water of the aqueous mixture and the aqueous mixture, the polar aprotic organic solvent and the azeotroping solvent form a salt-splitting liquid;
   heating the salt-splitting liquid to convert the (alkyl)ammonium 3-hydroxypropionate to 3-HP and ammonia, where heating the salt-splitting liquid produces a vapor phase containing at least water, ammonia and the azeotroping solvent;
   removing at least a portion of the water and the ammonia from the vapor phase during the heating; and
   returning at least a portion of the azeotroping solvent from the vapor phase back to the salt-splitting liquid to maintain the azeotrope mixture with the water of the aqueous mixture.

2. The process of claim 1, where the (alkyl)ammonium 3-hydroxypropionate is ammonium 3-hydroxypropionate (A3HP).

3. The process of claim 1, including heating the salt-splitting liquid to a temperature of 100° C. to 200° C.

4. The process of claim 1, where the azeotroping solvent is selected from the group consisting of toluene, m-xylene, anisole, methyl isobutyl ketone, benzene, cyclohexane, diethyl ether, methyl ethyl ketone or a combination thereof.

5. The process of claim 1, where returning at least a portion of the azeotroping solvent from the vapor phase back to the salt-splitting liquid includes maintaining a base level of at least 0.1 weight percent (wt. %) of the azeotroping solvent based on the total weight of the salt-splitting liquid.

6. The process of claim 5, where returning at least a portion of the azeotroping solvent from the vapor phase back to the salt-splitting liquid includes maintaining a base level of at least 1 wt. % of the azeotroping solvent based on the total weight of the salt-splitting liquid.

7. The process of claim 1, where a weight ratio of 3-HP to polar aprotic organic solvent (3-HP:polar aprotic organic solvent) in the aqueous mixture is 0.6:1 or lower.

8. The process of claim 1, where a weight ratio of 3-HP to polar aprotic organic solvent (3-HP:polar aprotic organic solvent) in the aqueous mixture is 0.18:1 to 0.58:1.

9. The process of claim 1, where the polar aprotic organic solvent is selected from the group consisting of dimethylformamide (DMF), dimethylacetamide (DMA), N-methyl-2-pyrrolidone (NMP), dimethyl sulfoxide (DMSO), dimethylsulfone, dioxane, diglyme, or a combination thereof.

10. The process of claim 1, where the polar aprotic organic solvent is dimethyl sulfoxide (DMSO) and the azeotroping solvent is toluene.

11. An salt-splitting liquid, comprising:
   an aqueous mixture including, water, (alkyl)ammonium 3-hydroxypropionate and 3-hydroxypropionic acid (3-HP);
   a polar aprotic organic solvent in which the water, the (alkyl)ammonium 3-hydroxypropionate and the 3-HP are soluble; and
   an azeotroping solvent, where the azeotroping solvent forms an azeotropic mixture with water of the aqueous mixture.

12. The salt-splitting liquid of claim 11, where the (alkyl) ammonium 3-hydroxypropionate is ammonium 3-hydroxypropionate (A3HP).

13. The salt-splitting liquid of claim 11, where the azeotroping solvent is selected from the group consisting of toluene, m-xylene, anisole, methyl isobutyl ketone, benzene, cyclohexane, diethyl ether, methyl ethyl ketone or a combination thereof.

14. The salt-splitting liquid of claim 11, where the salt-splitting liquid has a base level of at least 0.1 weight percent (wt. %) of the azeotroping solvent based on the total weight of the salt-splitting liquid.

15. The salt-splitting liquid of claim 11, where the salt-splitting liquid has a base level of at least 1 wt. % of the azeotroping solvent based on the total weight of the salt-splitting liquid.

16. The salt-splitting liquid of claim 11, where a weight ratio of 3-HP to polar aprotic organic solvent (3-HP:polar aprotic organic solvent) in the aqueous mixture is 0.6:1 or lower.

17. The salt-splitting liquid of claim 11, where the polar aprotic organic solvent is selected from the group consisting of dimethylformamide (DMF), dimethylacetamide (DMA), N-methyl-2-pyrrolidone (NMP), dimethyl sulfoxide (DMSO), dimethylsulfone, dioxane, diglyme, or a combination thereof.

18. The salt-splitting liquid of claim 11, where the polar aprotic organic solvent is dimethyl sulfoxide (DMSO) and the azeotroping solvent is toluene.

\* \* \* \* \*